US00PP35510P2

(12) United States Plant Patent
Hartman

(10) Patent No.: US PP35,510 P2
(45) Date of Patent: Nov. 28, 2023

(54) ***CALADIUM* PLANT NAMED 'WON OF14-1288'**

(50) Latin Name: ***Caladium* X *hortulanum***
Varietal Denomination: WON OF14-1288

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 18/121,524

(22) Filed: Mar. 14, 2023

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — C. Anne Whealy

(57) ABSTRACT

A new and distinct cultivar of *Caladium* plant named 'WON OF14-1288', characterized by its compact and mounding plant habit; dense, leafy and bushy appearance; vigorous growth habit and rapid growth rate; lance-type leaves that are medium green in color with white and creamy white-colored intervenous areas and pale green-colored venation; and petioles that are green to tannish green in color with brown-colored stippling and streaks.

4 Drawing Sheets

Figure 1:
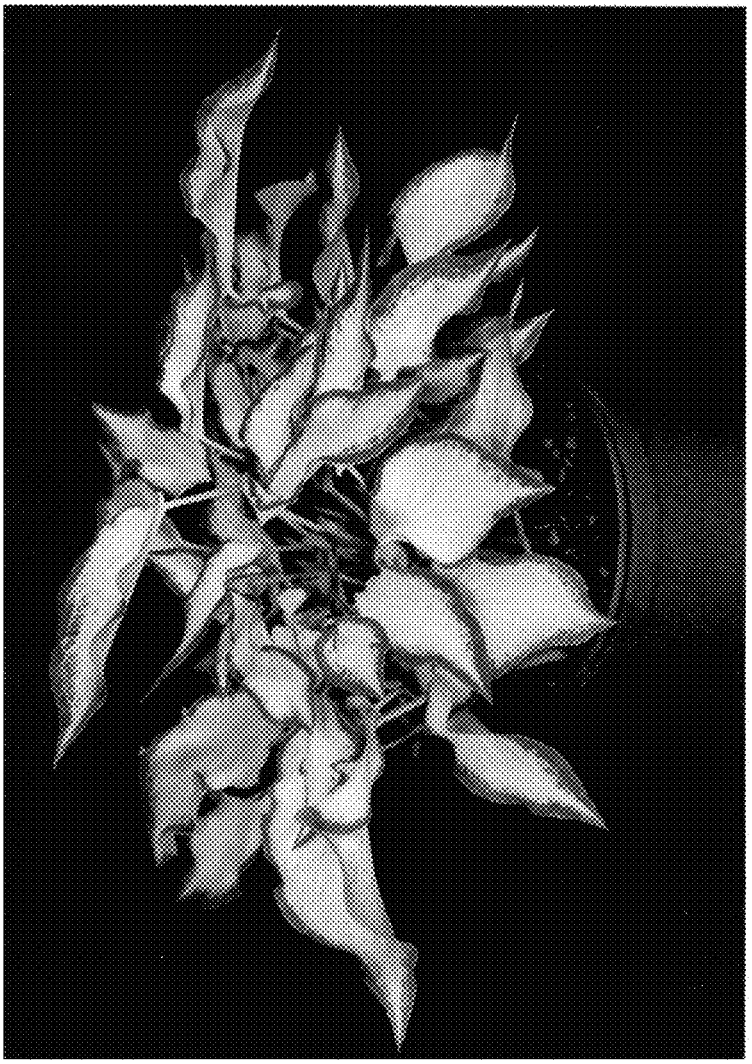

Botanical designation: *Caladium* X *hortulanum*.
Cultivar denomination: 'WON OF14-1288'.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'WON OF14-1288'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2013 in Avon Park, Fla. of *Caladium* X *hortulanum* 'RS-03-03', disclosed in U.S. Plant Pat. No. 26,265, as the female, or seed, parent with *Caladium* X *hortulanum* 'White Wonder', disclosed in U.S. Plant Pat. No. 21,044, as the male, or pollen, parent. The new *Caladium* plant was discovered and selected by the Inventor as a single plant within the progeny of the stated cross-pollination in a controlled outdoor nursery environment in Avon Park, Fla. in September, 2014.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2015 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'WON OF14-1288'. These characteristics in combination distinguish 'WON OF14-1288' as a new and distinct *Caladium* plant:

1. Compact, relatively short in height and mounding plant habit; dense, leafy and bushy appearance.
2. Vigorous growth habit and rapid growth rate.
3. Lance-type leaves that are medium green in color with white and creamy white-colored intervenous areas and pale green-colored venation.
4. Petioles that are green to tannish green in color with brown-colored stippling and streaks.

Plants of the new *Caladium* differ primarily from plants of the female parent, 'RS-03-03', in leaf color as leaves of plants of the new *Caladium* medium green in color with white and creamy white-colored intervenous areas and pale green-colored venation whereas leaves of plants of 'RS-03-03' are pearlescent white to greenish white in color with dark green-colored margins and white to greenish white-colored venation.

Plants of the new *Caladium* differ primarily from plants of the male parent, 'White Wonder', in the following characteristics:

1. Plants of the new *Caladium* are more mounding than and not as upright as plants of 'White Wonder'.
2. Leaves of plants of the new *Caladium* medium green in color with white and creamy white-colored intervenous areas and pale green-colored venation whereas leaves of plants of 'White Wonder' are white to grey-green in color with light pink to white-colored venation and dark green-colored borders.

Plants of the new *Caladium* can be compared to plants of *Caladium* X *hortulanum* 'White Delight', disclosed in U.S. Plant Pat. No. 21,216. In side-by-side comparisons, plants of the new *Caladium* differ primarily from plants of 'White Delight' in the following characteristics:

1. Plants of the new *Caladium* are shorter than plants of 'White Delight'.
2. Leaves of plants of the new *Caladium* medium green in color with white and creamy white-colored intervenous areas and pale green-colored venation whereas leaves of plants of 'White Delight' are white to grey-green in color with white-colored main veins and dark green-colored borders.
3. Leaf petioles of plants of the new *Caladium* are green to tannish green in color with brown-colored stippling and streaks whereas leaf petioles of plants of 'White Delight' are dark greenish brown with darker brown-colored stippling and tessellations.

Plants of the new *Caladium* can also be compared to plants of *Caladium* X *hortulanum* 'White Dynasty', disclosed in U.S. Plant Pat. No. 22,240. In side-by-side comparisons, plants of the new *Caladium* differ primarily from plants of 'White Dynasty' in the following characteristics:

1. Plants of the new *Caladium* are shorter and more mounding than plants of 'White Dynasty'.
2. Leaves of plants of the new *Caladium* medium green in color with white and creamy white-colored intervenous areas and pale green-colored venation whereas leaves of plants of 'White Dynasty' are white and greyed green with few random red purple-colored spots, dark green-colored margins and greyed green-colored venation.
3. Leaf petioles of plants of the new *Caladium* are green to tannish green in color with brown-colored stippling and streaks whereas leaf petioles of plants of 'White Dynasty' are green in color tinged with green and purplish brown-colored stippling and tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'WON OF14-1288' grown in a container that has had its tuber de-eyed prior to planting.

Figure 2:
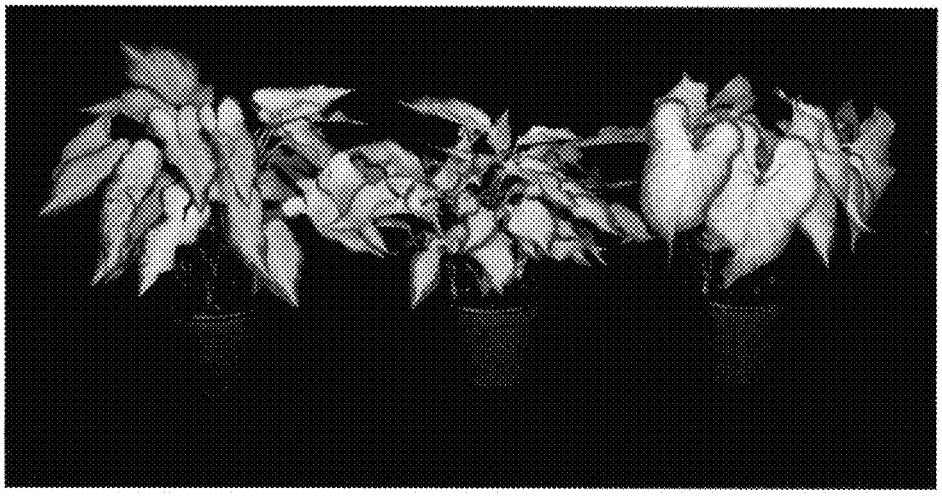

The photograph at the top of the second sheet (FIG. 2) is side perspective view of typical plants of the female parent, 'RS-03-03' (left), 'WON OF14-1288' (center) and the male parent, 'White Wonder' (right).

Figure 3:
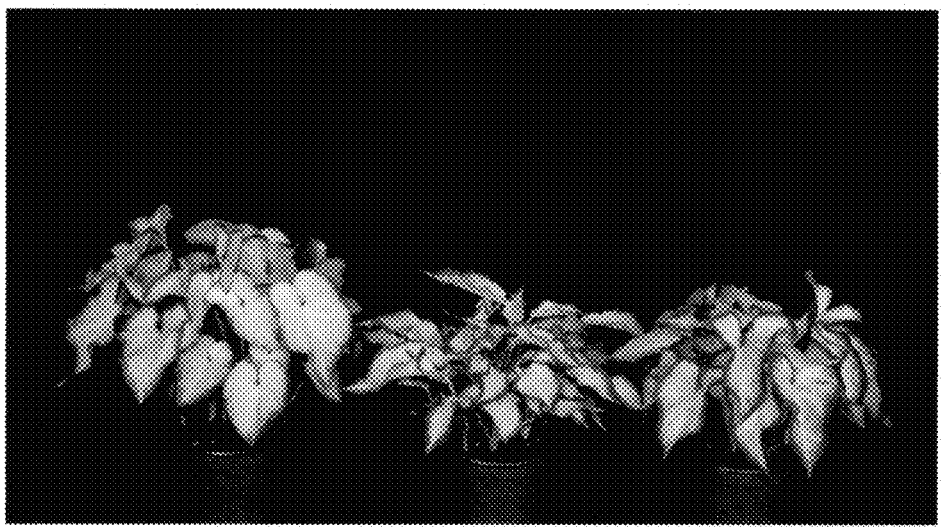

The photograph at the bottom of the second sheet (FIG. 3) is side perspective view of typical plants of 'White Delight' (left), 'WON OF14-1288' (center) and 'White Dynasty' (right).

Figure 4:
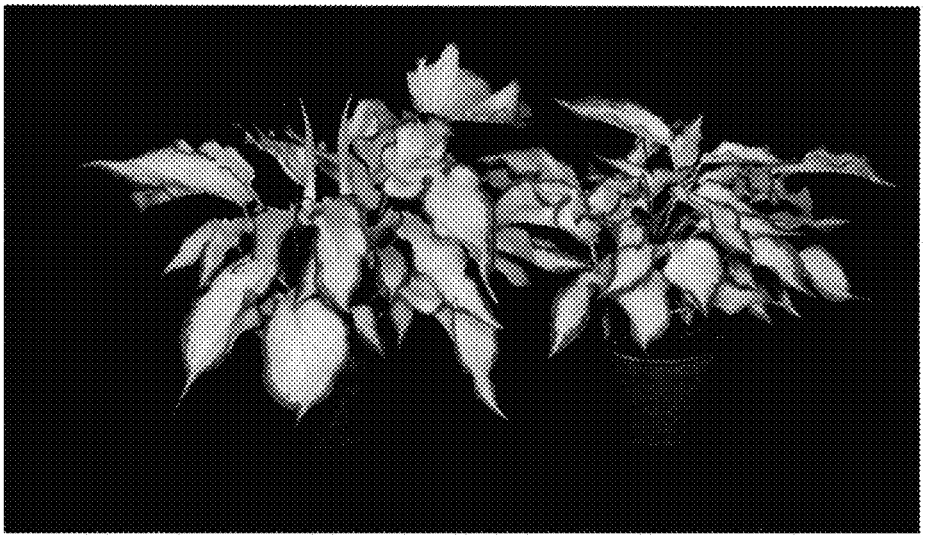

The photograph at the top of the third sheet (FIG. 4) is a comparison view of typical plants of 'WON OF14-1288' grown in containers, the plant on the left has not had its tuber de-eyed and the plant on the right has had its tuber de-eyed prior to planting.

Figure 5:
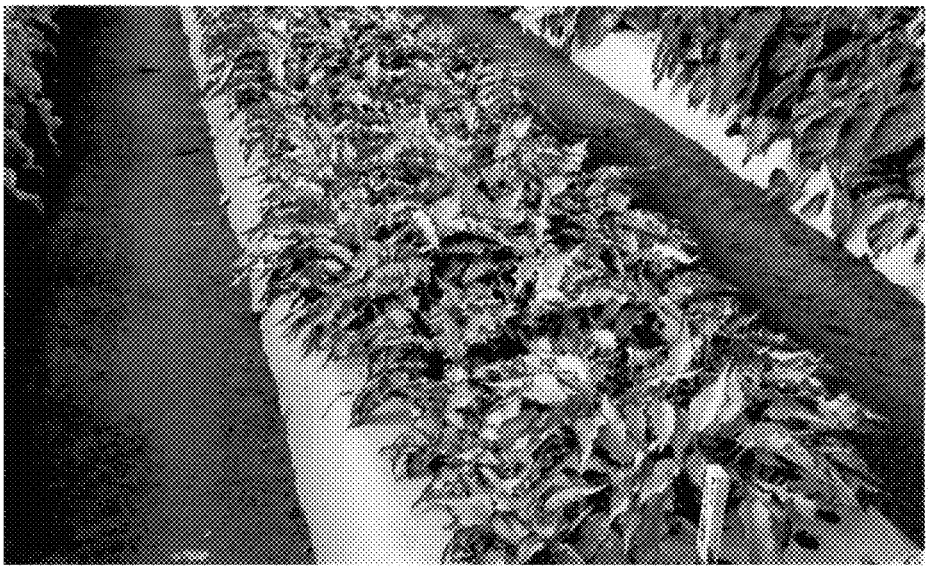

The photograph at the bottom of the third sheet (FIG. 5) is a side perspective view of typical plants of 'WON OF14-1288' grown in an open production field.

Figure 6:
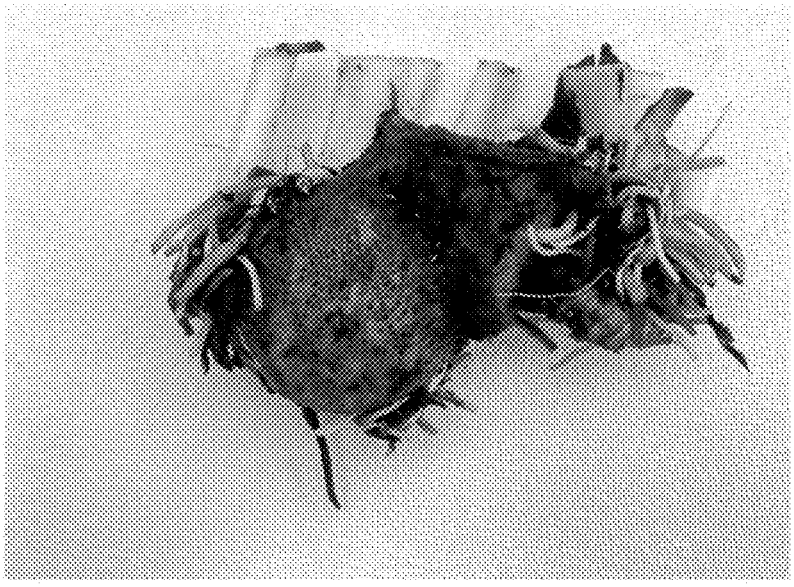

The photograph at the top of the fourth sheet (FIG. 6) is a close-up view of typical freshly-harvested tubers with roots and leaf petioles of 'WON OF14-1288'.

Figure 7:
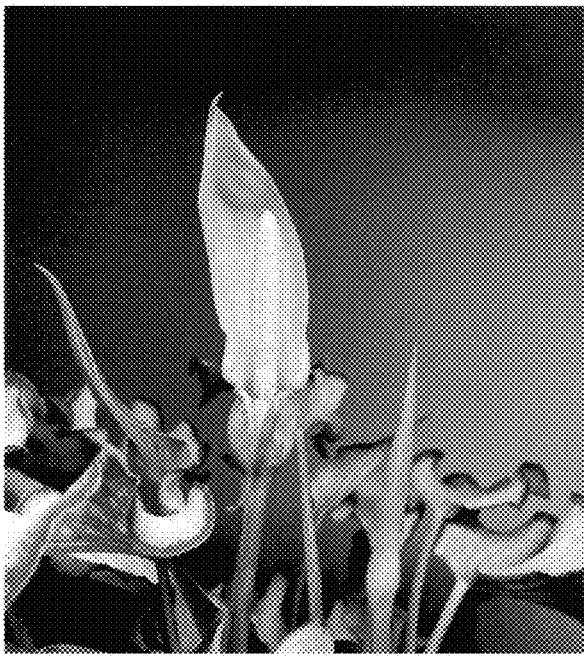

The photograph at the bottom of the fourth sheet (FIG. 7) is a close-up view of a typical flowering plant of 'WON OF14-1288'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28C to 33C, night temperatures ranged from about 22C to 25C and light levels were about 1,300 μmol. During the production of the outdoor nursery-grown plants, day temperatures ranged from about 29C to 35C, night temperatures ranged from about 23C to 26C and full sunlight conditions. Plants grown in the shade house were seven weeks old and plants grown in the outdoor nursery were 5.5 months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'WON OF14-1288'.

Parentage:

*Female, or seed, parent.*—*Caladium* X *hortulanum* 'RS-03-03', disclosed in U.S. Plant Pat. No. 26,265.

*Male, or pollen, parent.*—*Caladium* X *hortulanum* 'White Wonder', disclosed in U.S. Plant Pat. No. 21,044.

Propagation:

*Type.*—By "chipping" the tubers.

*Time to initiate roots, summer.*—About seven to ten days at temperatures about 32C.

*Time to initiate roots, winter.*—About two to three weeks at temperatures about 24C.

*Tuber description* (*outdoor nursery-grown plants*).—Appearance: Multi-segmented and branched; individual segments are ovate to irregular in shape. Height: About 2.9 cm to 3.4 cm. Diameter: About 3.7 cm to 4.8 cm. Segment height: About 2.6 cm to 2.8 cm. Segment diameter: About 1.6 cm to 1.8 cm. Axillary bud shape: Roughly triangular. Axillary bud height: About 6.5 mm. Axillary bud width: About 6 mm. Texture: Thick, starchy; somewhat brittle. Color: Periderm, freshly-harvested: Close to 174B. Periderm, dried: Close to 200A. Epidermis: Close to 200C to 200D. Cortical tissue: Close to 8D. Axillary buds: Close to 36D. Root description: Thick, fleshy contractile roots with few lateral branches; color, close to N155D occasionally tinged with close to 38D; actual color of the roots is dependent on substrate composition, water quality, fertilizer type and formulation, substrate temperature and physiological age of roots. Rooting habit: Moderately dense.

Plant description:

*Plant type.*—Herbaceous perennial; suitable as a potted plant in containers 15-cm to 25-cm and suitable as a landscape plant in shaded areas.

*Plant and growth habit.*—Compact, relatively short in height and mounding plant habit; dense, leafy and bushy appearance; vigorous growth habit and rapid growth rate; potted plants finish in saleable form in about seven weeks after planting tubers; leaf petioles and leaves arise from one or more growing points on tubers; leaf petioles initially upright and leaning outwardly with development.

*Plant height, from soil level to top of foliar plane, shade house-grown potted plants.*—About 20 cm to 27 cm.

*Plant height, from soil level to top of floral plane, shade house-grown potted plants.*—About 30.5 cm.

*Plant diameter, shade house-grown potted plants.*—About 38 cm to 47 cm.

*Number of shoots per plant, shade house-grown potted plants, tubers de-eyed.*—About 8 to 15 develop per #1 tuber.

*Number of shoots per plant, shade house-grown potted plants, tubers not de-eyed.*—About six to ten develop per #1 tuber.

*Cataphylls, shade house-grown potted plants.*—Length: About 4.5 cm. Width: About 1.1 cm. Shape: Wedge-shaped. Apex: Acuminate to emarginate. Base: Sheathing the stem. Texture, outer and inner surfaces: Smooth, glabrous. Color, outer surface: Close to 194D, streaked and stippled with close to 147A and tinged with close to 200B; may be variably and faintly tinged with close to 177D; color becoming closer to 199A and 200C with subsequent development. Color, inner surface: Close to N155C; colors and color patterns visible from outer surface visible.

Leaf description:

*Arrangement and type.*—Alternate; simple; lance-type.

*Length, shade house-grown potted plants.*—About 13.4 cm to 17 cm.

*Width, shade house-grown potted plants.*—About 6 to 7.8 cm; when flattened, about 7.5 cm to 8.4 cm.

*Shape.*—Ovate to lanceolate.

*Apex.*—Acuminate.

*Base.*—Sagittate.

*Margin.*—Entire; moderately wavy with broad undulations.

*Texture and luster, upper surface.*—Smooth, glabrous; thin; dull sheen.

*Texture and luster, lower surface.*—Smooth, glabrous; slightly glaucous around midvein and lateral venation; dull sheen.

*Venation pattern.*—Pinnate and palmate.

*Color, shade house-grown potted plants.*—When developing and fully expanded leaves, upper surface: Ground color: Close to NN137A and 194C. Center: Close to NN155C and 155C. Margins: Close to NN137A; edges, close to 147D. Basal notch: Tinged with close to 187B. Midvein: Close to 192A streaked with close to 194B. Lateral venation: Close to 192A streaked with close to 194B. When developing and fully expanded leaves, lower surface: Ground color: Close to 146D, 191A and 145D. Center: Close to 155C and 145D. Margins: Close to 191A; edges, close to 147D. Basal notch: Faintly tinged with close to 187B. Midvein: Close to 194C with faint streaks, close to 147C. Lateral venation: Close to 194C with streaks, close to 145B to 145C.

*Petioles.*—Aspect: Initially upright and straight and leaning outwardly with development; flexible. Length, shade house-grown potted plants: About 16.5 cm to 21.5 cm. Diameter, distally, shade house-grown potted plants: About 3 mm to 4 mm. Diameter, proximally, shade house-grown potted plants: About 4 mm to 6.5 mm. Texture: Smooth, glabrous; slightly glaucous. Color, shade house-grown potted plants: Close to 199D or 147C with stippling and streaks, close to 147B to 147C tinged with close to 200C; just below the leaf junction, close to 147C to 147D faintly stippled and streaked with close to 200C. Wing length, shade house-grown potted plants: About 4 cm to 6 cm. Wing diameter, shade house-grown potted plants: About 6 mm. Texture and luster, inner and outer surfaces: Smooth, glabrous; dull sheen. Wing color, shade house-grown potted plants: Outer surface: Close to 194D, stippled and streaked with close to 147A tinged with close to 200B; may be variably and faintly tinged with close to 177D. Inner surface: Close to N155C; colors and patterns on the outer surface are visible on the inner surface.

Inflorescence description:

*Inflorescence arrangement.*—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance.*—Night-fragrant; jasmine-like with camphor note.

*Natural flowering season and flower longevity.*—Plants of the new *Caladium* typically flower during the spring and summer in central Florida; flowers develop about eight weeks after growth commences; inflorescences last about three days before fading; inflorescences persistent.

*Spathe.*—Length, overall: About 14 cm. Length, distal open portion: About 11 cm. Length, proximal closed portion: About 3 cm. Width, distal open portion: About 3.1 cm. Depth, distal open portion: About 6 cm. Width, at constriction: About 1.6 cm. Width, proximal closed portion: About 2.1 cm. Shape, open portion: Ovate to lanceolate. Apex: Acuminate. Base: Acute. Margin: Entire; not undulate. Texture and luster, front surface: Smooth, glabrous; dull sheen. Texture and luster, rear surface: Smooth, glabrous; slightly glaucous. Color, front surface: Distal open portion: Close to 157D and 145D; with subsequent development, distally becoming closer to 199B and 200C. Proximal closed portion: Close to 148D, with sparse and faint blotches, close to N186C; color does not change with subsequent development. Color, rear surface: Distal open portion: Close to 145C and 145D; central area, streaked with close to 147C to 147D; color does not change with subsequent development. Proximal closed portion: Close to 147D and 148D with streaks, close to 147C; color does not change with subsequent development.

*Spadix.*—Length, overall: About 7.3 cm. Length, male flower zone: About 3.8 cm. Length, sterile zone: About 1.5 cm. Length, female flower zone: About 2 cm. Diameter, male flower zone: About 8 mm. Diameter, sterile flower zone: About 5 mm. Diameter, female flower zone: About 8 mm. Shape: Columnar, spindle-shaped. Apex: Obtuse, rounded. Base: Obtuse. Aspect: Upright. Color, mature, male zone: Close to 159D. Color, mature, sterile zone: Close to 155D. Color, mature, female zone: Close to 159C and 159D. Male flowers: Quantity per spadix: About 90. Shape: Obovate. Height: About 3.5 mm. Diameter: About 3 mm to 3.5 mm. Pollen amount: Abundant. Pollen color: Close to 10C. Female flowers: Quantity per spadix: About 168. Shape: Obovate. Height: About 3 mm. Diameter: About 2 mm. Stigma color: Close to 159D. Ovary color: Close to 159C.

*Scapes.*—Length: About 16 cm. Diameter: About 5 mm. Strength: Sturdy; flexible. Aspect: Mostly erect, straight. Texture and luster: Smooth, glabrous; slightly glossy and distally, glaucous. Color: Close to 147A tinged with close to N199B; just below spathe, close to 147B.

*Seeds and fruits.*—To date, seed and fruit development have not been observed on plants of the new *Caladium.*

Pathogen tolerance/resistance: Plants of the new *Caladium* have been observed to have average tolerance to *Pythium* Root Rot and above average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7C to about 40C and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'WON OF14-1288' as illustrated and described.

* * * * *